(12) United States Patent
Ganemo

(10) Patent No.: US 6,399,082 B1
(45) Date of Patent: Jun. 4, 2002

(54) MIXTURE OF A DIOL AND AN ALPHA-HYDROXY ACID FOR THE TREATMENT OF HYPERKERATOTIC SKIN DISEASES

(75) Inventor: Agneta Ganemo, Munka Ljunby (SE)

(73) Assignee: Yamanouchi Europe B.V., Leiderdrop (NL)

( * ) Notice: Subject to any disclaimer, the term of this patent is extended or adjusted under 35 U.S.C. 154(b) by 0 days.

(21) Appl. No.: 09/554,330

(22) PCT Filed: Nov. 25, 1998

(86) PCT No.: PCT/EP98/07759

§ 371 (c)(1),
(2), (4) Date: Jun. 27, 2000

(87) PCT Pub. No.: WO99/26617

PCT Pub. Date: Jun. 3, 1999

(30) Foreign Application Priority Data

Nov. 25, 1997 (EP) .............................. 97203681

(51) Int. Cl.⁷ ............................ A61K 7/00; A61K 7/40; A61K 7/48; A61K 9/14; A61K 9/10

(52) U.S. Cl. ........................ 424/401; 424/489; 424/502; 514/846; 514/847

(58) Field of Search ................................ 424/401, 489, 424/502; 514/846, 847

(56) References Cited

U.S. PATENT DOCUMENTS

| | | | | |
|---|---|---|---|---|
| 4,105,783 A | * | 8/1978 | Yu et al. | 424/283 |
| 5,407,958 A | * | 4/1995 | Heath et al. | 424/28.06 |
| 5,525,635 A | * | 6/1996 | Moberg | 514/588 |
| 5,665,366 A | * | 9/1997 | Rawlings et al. | 424/401 |
| 5,667,800 A | * | 9/1997 | De Vringer | 424/450 |

OTHER PUBLICATIONS

Eugene J. Van Scott, et al. "Hyperkeratinization, Corneocyte Cohesion, Alpha Hydroxy Acids," *Journal of the American Academy of Dermatology*. 11: 867–879, 1984.

* cited by examiner

Primary Examiner—Thurman K. Page
Assistant Examiner—Rachel M. Bennett
(74) Attorney, Agent, or Firm—McDonnell Boehnen Hulbert & Berghoff

(57) ABSTRACT

The use of compositions containing a mixture of a diol and an alpha-hydroxy acid in a semi-occluding vehicle for the topical treatment of hyperkeratotic skin diseases is provided.

16 Claims, No Drawings

MIXTURE OF A DIOL AND AN ALPHA-HYDROXY ACID FOR THE TREATMENT OF HYPERKERATOTIC SKIN DISEASES

This application is a 371 of PCT/EP98/07759 filed Nov. 25,1998.

The present invention relates to the use of a combination of a diol and an alpha-hydroxy acid for the topical treatment of hyperkeratotic skin diseases.

BACKGROUND OF THE INVENTION

Chronic hyperkeratotic skin diseases are characterised by a disturbance in the keratinisation process and include among other diseases psoriasis, hyperkeratotic eczema and ichthyosis.

Psoriasis is characterised by reddened flaking skin lesions. The disease, has as a rule, a chronic course. Topical agents for the treatment thereof are often smeary and or discoloring, e.g. dithranol and tar. Steroid preparations are cosmetically attractive but have important side-effects. Emollient preparations containing e.g. salicylic acid and urea in a cream or ointment base have a certain peeling effect but are not separately sufficiently active.

Hyperkeratotic eczema is characterised by thickened scaling skin often with chaps (rhazades).

Lamellar ichthyosis is a rare congenital genodermatosis characterised by generalised hyperkeratosis intense dryness of the skin and large scales especially over the extremities (H. Traupe, ed. (1989) The Ichthyoses: A guide to clinical diagnosis, genetic counseling and therapy, 1st ed., Springer Verlag, Berlin). Though usually not life-threatening, the disease can be very disfiguring and causes considerable distress to the sufferers throughout life. The treatment of lamellar ichthyosis involves oral vitamin A derivatives (retinoids) combined with adjuvant topical treatment with different emollient formulations containing e.g. urea, propylene glycol and alpha-hydroxy acids (AHA). However, the therapeutic results like in other hyperkeratotic skin diseases, are often disappointing and associated with side-effects.

E. J. Van Scott et al. (1974) Arch. Derrnatol. 110: 586–590 pioneered in using alpha-hydroxy acids against ichthyotic conditions. Further E. J. Van Scott et al. (1984) J. Am. Acad. Dermatol. 11: 867–879 described a keratolytic gel (5–10% alpha-hydroxy acid in a vehicle consisting of water, ethanol and propylene glycol (4:4:2), which however fell in oblivion since it was irritating and not suitable for whole body application.

In EP-0292495 compositions, consisting essentially of a mixture of propylene glycol, urea and optionally lactic acid, were disclosed. The compositions after topical application to the skin were said to have a beneficial effect on hyperkeratotic skin diseases. Simple application of the said mixture to the skin is possible, but in practice proved to be very difficult to achieve effectively. The mixture is fluid and slow to dry (evaporate) and the use of plasters and/or bandages is deemed necessary. This procedure is considered to be too inconvenient for general use. Besides that, due to the high concentrations of propylene glycol (40–80%) and urea (5–20%), side-effects, such as irritation, may occur, which also are a serious draw-back for daily application of such preparations during a prolonged period of time.

U.S. Pat. No. 4,105,783 discloses compositions containing a product, prepared by reacting, in aqueous or alcoholic aqueous solution, one or more of an alpha-or a beta-hydroxy acid and a base selected from the group consisting of ammonium hydroxide and an organic alkylamine, in a total amount of from 1 to 20% for the topical treatment of dry skin disorders, such as psoriasis and ichthyosis. The bases are successfully used to raise the pH of the compositions containing the hydroxy acids without compromising the therapeutic activity of the active ingredients, thereby reducing the skin irritation. Although it was stated that the reaction products, viz the ammonium salts and amides, thus formed, need no isolation procedure and can be directly incorporated into the therapeutic composition, good manufacturing and clinical practices nowadays require a careful assessment of the active ingredient both qualitatively and quantitatively and extensive pharmacological and toxicological testing of the reaction product formed.

There thus still exists a need for an effective product based on well-known and well-defined active ingredients or a method which can be topically applied to hyperkeratotic skin without causing serious side-effects, such as irritation.

SUMMARY OF THE INVENTION

The object of the present invention is to provide the use of compositions containing a combination of a diol and an alpha-hydroxy acid in a vehicle, which has semi-occluding properties, for topical treatment of hyperkeratotic skin diseases.

DETAILED DESCRIPTION OF THE INVENTION

It has now been found that compositions containing a combination of a diol and an alpha-hydroxy acid in a semi-occluding vehicle on topical application to the skin of patients, having a hyperkeratotic skin disease, are effective and show a considerable reduction of side-effects, such as irritation, as compared with compositions, containing the same amounts of the diol and the alpha-hydroxy acid in a non-occluding vehicle, such as a gel. In addition thereto the compositions of the invention show a remarkably greater efficacy than compositions comprising either the diol or the alpha-hydroxy acid in the same amount.

Examples of diols which may be used are propylene glycol, butylene glycol, pentanediol and hexylene glycol. There is a preference for propylene glycol and hexylene glycol, which may be used in a concentration of up to 40% and preferably from 10–20%.

Examples of the alpha-hydroxy acids or derivatives thereof are lactic acid, citric acid, glycolic acid, glucuronic acid, galacturonic acid, pyruvic acid etc, but preferably lactic acid is used. The alpha-hydroxy acid may be used in an amount of up to 10%, but preferably up to 5% is used.

The semi-occluding vehicles to be used are characterised by the fact that in in vitro and in vivo tests an occluding activity is observed, which is lower than for white soft paraffin, which is considered to be an occluding vehicle. The lower limit for the occluding activity is determined by values which are obtained for preparations, known to be non-occluding. E.g. in the in vitro test as disclosed in example 7 preparations having an occlusion factor below about 70 are considered to be non-occluding preparations. A proper in vivo test, wherein the effectiveness of topical preparations in restoring a cutaneous barrier function of diseased skin is assessed, is disclosed in example 8. Examples of such semi-occluding vehicles are fatty creams, containing a certain amount of occluding fats, such as white soft paraffin, or creams, containing an aqueous suspension of solid lipid nanoparticles, e.g. wherein the solid lipid is hard paraffin, having a melting point range from 54 to 57° C.

The combination of only 5% lactic acid and 20% propylene glycol in a fatty cream base is readily acceptable by most patients and has proved to be much more effective and less irritating than monotherapy with either of the two compounds in the same or even at twice these concentrations. The astonishingly potent effect of the mixture of the diol and the alpha-hydroxy acid in the semi-occluding vehicle suggests that the ingredients act synergistically in reverting hyperkeratosis.

The compositions according to the invention can be used in several stages of the treatment of hyperkeratotic skin diseases. In the pretreatment of psoriatic plaques before initiation of treatment with e.g. corticosteroids the compositions have proven to be equally good as the standard product, which is 5% of salicylic acid in white soft paraffin. However, the cosmetic properties of the compositions according to the invention were considered by the patients to be superior over those of the standard product. The treatment of lamellar ichthyosis normally consists of systemic therapy with retinoids combined with adjuvant topical treatment. The compositions according to the invention have proven to be advantageously used in such adjuvant topical treatment. For less severe hyperkeratotic skin disorders the compositions according to the invention can be used without systemic therapy.

Although the foregoing invention has been described in some detail by way of illustration and example for purposes of clarity and understanding, it will be readily apparent to those of ordinary skill in the art in the light of the teachings of this invention that certain changes and modifications may be made thereto without departing from the spirit and the scope of the appended claims.

The following examples further illustrate the invention.

EXAMPLES

Example 1

| | |
|---|---|
| lactic acid | 5% |
| propylene glycol | 20% |
| fatty cream base* | 75% |

*The fatty cream base consists of 3% polyoxyethylene 1000 monocetyl ether (Cetomacrogol ® 1000), 6% cetostearyl alcohol, 18% liquid paraffin, 42% white soft paraffin, preservatives q.s., buffers q.s. and water up to 100%.

Example 2

| | |
|---|---|
| lactic acid | 5% |
| propylene glycol | 20% |
| nanoparticles suspension* | 75% |

*The nanoparticles suspension consists of 30% solid paraffin (melting point range 54–57° C.), 5% polyoxyethylene 1000 monocetyl ether and 65% water.

Example 3

| | |
|---|---|
| lactic acid | 5% |
| propylene glycol | 20% |
| nanoparticles cream* | 75% |

*The nanoparticles cream consists of 2% cetyl dimethicone copolyol, 10% isopropyl myristate, 16.67% cyclomethicone, 0.33% sodium chloride, 10% solid paraffin, 1.67 polyoxyethylene 1000 monocetyl ether, buffers q.s., preservatives q.s. and water up to 100%.

Example 4

| | |
|---|---|
| lactic acid | 5% |
| propylene glycol | 20% |
| cream* | 65% |

*The cream consists of 32.5% cetostearyl alcohol, 5% polyoxyethylene 1000 monocetyl ether and 62.5% water.

Example 5

| | |
|---|---|
| lactic acid | 5% |
| propylene glycol | 20% |
| nanoparticles suspension/ cream (2.5/1)* | 65% |

*The vehicle consists of a mixture of the nanoparticles suspension of example 2 and the cream of example 4.

Example 6

Ten patients (7 females; age 2–38 years) with severe lamellar ichthyosis, two of whom had ongoing treatment with oral acitretin (50–75 mg/day) were recruited after informed consent. The patients were instructed to apply the formulation according to example 1 twice daily to the legs and refrain from any other topical medication at that side. Signs of scaling, hyperkeratosis and xerosis were separately scored on a scale ranging from 0 (feature not present) to 4 (feature present to a large extent) and the sums of the scores for these features (max.: 12) were calculated for each patient before and after changing therapy. Use of the formulation according to example 1 resulted after 1 month in a reduction of the mean total score from 9.6±2.2 to 3.5±2.3 ($p<0.001$; paired t-test). All patients reported increased shredding of scales after a few days of treatment, followed within 1–2 weeks by the appearance of a much smoother, almost normal looking skin. Nine patients considered the effect "better than ever obtained before" and later choose to extend the treatment to the rest of the body with equally good results. Hence one patient was able to reduce her acitretin dosage from 75 mg to 25 mg daily without deterioration of skin symptoms. Some patients experienced a transient skin irritation after applying the cream. No other side effects were noted.

Example 7

A vessel in the form of a beaker was used. The vessel had a diameter of 5.5. cm and a height of 7 cm, and had been designed to receive on top a closing standard laboratory paper filter (TVN, sold by Schut, the Netherlands, surface 23.8 cm$^2$). The test was performed by placing 50 g of distilled water in the vessel, closing the vessel with the paper filter on the upper surface of which 200 mg of the preparation to be tested were evenly distributed, and placing the closed vessel for a period of 72 hours in a stove at 33° C. and 58% RH. All other conditions having been kept equal, the weight loss of water from the vessel (water flux) after 72 hours exclusively depended on the occlusivity of the preparation tested.

The occlusion factor F of the tested preparation was calculated according to the equation:

$$F=100\{(A-B)A\}$$

wherein A is the water flux through the uncovered filter and B the water flux through the filter when covered by the tested preparation.

All preparations were tested in triplicate, the maximal deviation between the results of one preparation being 10%. The following table presents the means of the occlusion factors F found.

| Vehicle of example | Occlusion Factor F |
|---|---|
| 1 | 91.7 |
| 2 | 78.5 |
| 4 | 73.0 |
| 5 | 87.0 |

Example 8

Hospitalised female patients (8) with chronic constitutional eczema were included in a study to assess the effectiveness of various topical preparations in restoring a cutaneous barrier function by means of Trans Epidermal Water Loss measurements. The flexor aspect of the right forearm was used throughout the study. The included sites (area in between a distance of about 5 cm from wrist to elbow) were examined to be classified as light, moderate or severely affected. The patients were not allowed to use any topical medication 24 hours before commencement of the study. The experiments were performed in a separate room with constant humidity and temperature. These parameters were checked before the start of the experiments. The patients were quietly seated for at least 10 minutes prior to the start of the measurements. The measurements were carried out using a Servo Med EP1 Evaporimeter (Servo Med, Stockholm, Sweden), calibrated according to the manufacturers instructions. 6 areas of about 3×3 cm were indicated on the forearm of each patient, 0.5 ml of the preparations were applied on the indicated spots For each patient the preparations were applied at the same spot. After massaging for 0.5 minutes with a fingertip and a period of 2 minutes, the remaining of the preparations was discarded with a wooden scraper followed by gently wiping with a piece of tissue. The sixth spot was left untreated to allow control measurements. Initial TEWL-values were determined on each spot before application of the dressings (t=0 values). Accordingly, the indicated spots were measured at 0.5, 1, 1.5, 2; 3; 4; 6 and 8 hours after treatment. All measurements were conducted in triplicate.

The results showed that white soft paraffin is always the best preparation with respect to prevention of TEWL and can be considered as an occluding preparation. The vehicle of example 1 resulted in a lower normalisation of the skin barrier function than white soft paraffin, but the preparation can be considered to be semi-occluding.

What is claimed is:

1. A composition for the treatment of hyperkeratotic skin disease, the composition consisting essentially of an α-hydroxy acid, a diol, and a semi-occluding carrier vehicle.

2. The composition according to claim 1 wherein the diol is selected from the group consisting of propylene glycol, butylene glycol, pentane diol, and hexylene diol.

3. The composition according to claim 1 wherein the diol is present in concentration of 40% or less.

4. The composition according to claim 1 wherein the diol is present in concentration of 10%–20%.

5. The composition according to claim 1 wherein the α-hydroxy acid is selected from the group consisting of lactic acid, citric acid, glycolic acid, glucuronic acid, galacturonic acid and pyruvic acid.

6. The composition according to claim 1 wherein the α-hydroxy acid is present in concentration of 10% or less.

7. The composition according to claim 1 wherein the α-hydroxy acid is present in a concentration of 5% or less.

8. The composition according to claim 1 wherein the diol is propylene glycol, which is present in a concentration of 20% and the α-hydroxy acid is lactic acid, which is present in a concentration of 5%.

9. A method of treating hyperkeratotic skin disease comprising topically administering to a patient afflicted with a hyperkeratotic skin disease a composition according to claim 1.

10. A method of treating hyperkeratotic skin disease comprising topically administering to a patient afflicted with a hyperkeratotic skin disease a composition according to claim 2.

11. A method of treating hyperkeratotic skin disease comprising topically administering to a patient afflicted with a hyperkeratotic skin disease a composition according to claim 3.

12. A method of treating hyperkeratotic skin disease comprising topically administering to a patient afflicted with a hyperkeratotic skin disease a composition according to claim 4.

13. A method of treating hyperkeratotic skin disease comprising topically administering to a patient afflicted with a hyperkeratotic skin disease a composition according to claim 5.

14. A method of treating hyperkeratotic skin disease comprising topically administering to a patient afflicted with a hyperkeratotic skin disease a composition according to claim 6.

15. A method of treating hyperkeratotic skin disease comprising topically administering to a patient afflicted with a hyperkeratotic skin disease a composition according to claim 7.

16. A method of treating hyperkeratotic skin disease comprising topically administering to a patient afflicted with a hyperkeratotic skin disease a composition according to claim 8.

* * * * *